United States Patent [19]

Theissen

[11] 4,339,268

[45] Jul. 13, 1982

[54] HERBICIDAL NITROALKYL 5-[2-CHLORO-4-(TRIFLUOROMETHYL)-PHENOXY]-2-NITROBENZOATES

[75] Inventor: Robert J. Theissen, Bridgewater, N.J.

[73] Assignee: Rhone-Poulenc Agrochimie, Lyons, France

[21] Appl. No.: 271,143

[22] Filed: Jun. 8, 1981

Related U.S. Application Data

[63] Continuation-in-part of Ser. No. 117,732, Feb. 1, 1980, abandoned.

[30] Foreign Application Priority Data

Jan. 30, 1981 [AR] Argentina ............................... 284163

[51] Int. Cl.$^3$ ...................... A01N 37/36; C07C 79/46

[52] U.S. Cl. ........................................ 71/108; 560/21

[58] Field of Search ............................. 71/108; 560/21

[56] References Cited

U.S. PATENT DOCUMENTS 4,093,446  6/1978  Bayer et al. ........................... 560/21
4,263,041  4/1981  Grove ...................................... 71/108

Primary Examiner—G. T. Breitenstein
Attorney, Agent, or Firm—Morgan, Finnegan, Pine, Foley & Lee

[57] ABSTRACT

There is provided herbicidal nitroalkyl 5-[2-chloro-4-(trifluoromethyl)phenoxy]-2-nitrobenzoates. These compounds are particularly useful when applied in a post-emergence application to soybean fields containing broadleaf weeds.

8 Claims, No Drawings

HERBICIDAL NITROALKYL 5-[2-CHLORO-4-(TRIFLUOROMETHYL)PHENOXY]-2-NITROBENZOATES

CROSS REFERENCE TO RELATED APPLICATIONS

This application is a continuation-in-part of U.S. application Ser. No. 117,732, filed Feb. 1, 1980, now abandoned.

BACKGROUND OF THE INVENTION

The invention is concerned with herbicidal nitroalkyl 5-[2-chloro-4-(trifluoromethyl)phenoxy]-2-nitrobenzoates.

The compound, 5-[2-chloro-4-(trifluoromethyl) phenoxy]-2-nitrobenzoic acid, including the salt forms thereof, is known to have herbicidal activity. According to a particular herbicidal treatment, it has been proposed to apply this compound in a post-emergence fashion to control weeds, especially broadleaf weeds, in soybean fields. Accordingly, in such an application, a herbicide must possess the following two properties at the applied dosage rate: (1) the ability to control the target weeds; and (2) the ability to remain safe to the soybeans.

In attempting to improve on the herbicidal properties of 5-[2-chloro-4-(trifluoromethyl)phenoxy]-2-nitrobenzoic acid and salts thereof, various derivatives of these compounds have been proposed including alkyl and cycloalkyl esters, alkylthio esters, phenyl ester, alkyl and dialkyl amido and benzoyl chloride forms. U.S. Pats. which describe such compounds and the like include Nos. 3,652,645; 3,784,635; 3,873,302; 3,983,168; 3,907,866; 3,798,276; 3,928,416; and 4,063,929. For example, the simple methyl ester of the above-mentioned acid, i.e., methyl 5-[2-chloro-4-(trifluoromethyl)-phenoxy]-2-nitrobenzoate, has been proposed, and it has been discovered that this compound has even greater herbicidal activity than 5-[2-chloro-4-(trifluoromethyl)-phenoxy]-2-nitrobenzoic acid with respect to various weeds, e.g. broadleaf weeds. However, it has also been discovered that methyl 5-[2-chloro-4-(trifluoromethyl)-phenoxy]-2-nitrobenzoate has a relatively large degree of post-emergence herbicidal activity with respect to crops. Consequently, methyl 5-[2-chloro-4-(trifluoromethyl)phenoxy]-2-nitrobenzoate should not be applied in a post-emergence fashion to control broadleaf weeds in soybeans, because this compound tends to kill soybeans along with the weeds in such applications.

Accordingly, there is a need in the art for compounds which have a desirable combination of herbicidal properties with respect to weed activity and crop safety.

SUMMARY OF THE INVENTION

This invention provides certain herbicidal compounds of the formula:

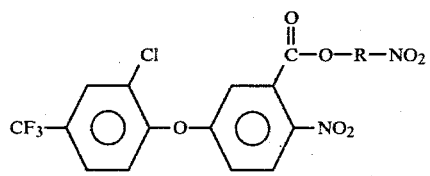

where R is an alkylene group having 1–4 carbon atoms.

The compounds of this class may be prepared by a variety of techniques such as, e.g., by displacement of an active halogen, e.g., halo-R—$NO_2$, with the salt of an acid, e.g.

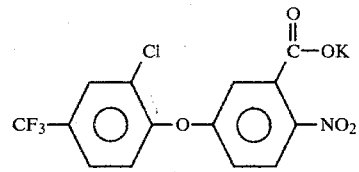

The following nitroalkyl esters as defined by Formula I were prepared:

| Compound | OR—$NO_2$ | m.p. °C. |
|---|---|---|
| 1 | —$OCH_2CH_2$—$NO_2$ | oil |
| 2 | —$OCH_2CH(CH_3)$—$NO_2$ | oil |
| 3 | —$OCH_2C(CH_3)_2$—$NO_2$ | |
| 4 | —$OCH(CH_3)CH_2$—$NO_2$ | oil |

Further, techniques for preparing the compounds of Formula I are illustrated by way of example, as follows:

EXAMPLE 1

Preparation of (2-methyl-2-nitropropyl) 5-[2-chloro-4-(trifluoromethyl)phenoxy]-2-nitrobenzoate.

To a stirred solution of 5-[2-chloro-4-(trifluoromethyl)phenoxy]-2-nitrobenzoyl chloride (3.8 g, 0.01 mole) in acetone (10 ml) was added 2-methyl-2-nitropropanol (1.19 g, 0.01 mole) in acetone (10 ml) followed by triethylamine (1.01 g, 0.01 mole) in acetone (5 ml). The temperature rose and a white precipitate formed. The reaction was heated to reflux for 2.5 hours and then stirred overnight at room temperature. After dilution with water (75 ml), the solution was extracted twice with methylene chloride (25 ml @). The organic solution was then washed with 5% sodium hydroxide and finally with a brine solution. The dried solution was concentrated to give an amber oil 2.83 g.

I.R. (neat): C=O, 1740 cm$^{-1}$ (broad)

NMR (CDCl$_3$): singlet 1.65 ppm (6 H), singlet 4.67 ppm (2 H), complex multiplet 7.1–8.0 (5 H), doublet 8.12 ppm (1 H, J=9.6 HZ).

EXAMPLE 2

Preparation of (2-nitropropyl) 5-[2-chloro-4-(trifluoromethyl)phenoxy]-2-nitrobenzoate.

A stirred mixture of 5-[2-chloro-4-(trifluoromethyl)-phenoxy]-2-nitrobenzoic acid (50 g, 0.139 mole), 2-nitropropanol (13.2 g, 0.126 mole) and conc. sulfuric acid (1 ml) in benzene (500 ml) was heated to reflux for 24 hours, during which time water (1.9 g) was removed via a Dean Stark trap. The solvent was stripped under reduced pressure and the residue poured into water (700 ml). The product was extracted into ether, which was washed with water and then with 5% sodium bicarbonate. The dried ether solution was concentrated to give 23.2 g of an amber oil which slowly solidified to a tacky semi-solid.

I.R. (neat): C=O 1740 cm$^{-1}$

NMR (CDCl$_3$): doublet 1.62 ppm (3 H, J=6.4 HZ), complex multiplet 4.6–5.2 ppm (3 H), complex multiplet 7.1–8.0 ppm (5 H), doublet 8.15 pm (1 H, J–10.0 HZ)

EXAMPLE 3

Preparation of (2-nitroethyl) 5-[2-chloro-4-trifluoromethyl)phenoxy]-2-nitrobenzoate.

According to the same procedure described in Example 2 there was obtained 24.0 g of the desired 2-nitroethyl ester as a thick amber oil.

I.R. (neat): C=O 1740 cm$^{-1}$

NMR (CDCl$_3$): complex multiplet 4.6–5.1 ppm (4 H); complex multiplet 7.1–8.0 ppm (5 H); doublet 8.15 ppm (1 H, J=10.0 HZ).

The compounds of this invention can be applied in various ways to achieve herbicidal action. They can be applied per se, as solids or in vaporized form, but are preferably applied as the toxic components in pesticidal compositions of the compound and a carrier. These compositions may be applied directly to the soil and often incorporated therewith. The compositions can be applied as granulars or dusts; as liquid sprays, or as gas-propelled sprays and can contain, in addition to a carrier, additives such as emulsifying agents, binding agents, gases compressed to the liquid state, odorants, stabilizers, and the like. A wide variety of liquid and solid carriers can be used. Non-limiting examples of solid carriers include talc, bentonite, diatomaceous earth, pyrophyllite, fullers earth, gypsum, flours derived from cotton seeds and nut shells, and various natural and synthetic clays having a pH not exceeding about 9.5. Non-limiting examples of liquid carriers include water, organic solvents such as alcohols, ketones, light oils, and medium oils and vegetable oils such as cottonseed oil.

In practice, herbicidal application is measured in terms of pounds of herbicide applied per acre. The compounds of this invention are effective herbicides when applied in herbicidal amounts, i.e., at rates between about 0.03 pound and about 10 pounds per acre.

Herbicidal Effectiveness

Method of Propagating Test Species

Crop and weed species are planted in 8"×10" disposable fiber flats containing potting soil to provide each flat with a 4" row of all test species. Crop species consist of field corn (CN), cotton (CT), and soybeans (SB). The weed species consist of foxtail millet (FM), green foxtail (GF), velvetleaf (VL), cocklebur (CB), wild mustard (WM) and pigweed (PW).

Cotton, corn, soybean, and cocklebur plantings consist of 4 to 5 seeds per row depending upon species. The smaller seeded species (velvetleaf, wild mustard, pigweed, foxtail millet and green foxtail) are planted in an uncounted but sufficient number to provide a solid row of seedlings.

Plantings for the pre- and post-emergence portions of the test are identical as to seeding. The initial watering until emergence is done from the top. The post-emergence phase is propagated in advance so as to provide plants of the proper stage of development at the time of treatment. Plantings for the pre-emergence phase are made not more than one day in advance of treatment.

The desired stage of development for treatment of the post-emergence broadleaf species (CT, SB, CB, VL, WM, PW) is the one true leaf or first trifoliate leaf stage. The desired stage for corn would be a height of 3–4", while a 2" height would be adequate for the grasses.

Method of Treatment

Spray applications are made with a handgun sprayer (aspirator type) simultaneously to one flat of established plants for the post-emergence phase and one newly seeded flat for the pre-emergence phase. A 10 lb./acre treatment rate consists of the uniform application of 116 milligrams of test compound to the combined area of the two flats (160 sq. inches). Application is made in a solvent mixture consisting of 40 ml acetone and 40 ml water and a surfactant concentration of 0.1 percent.

Following spray application, flats are returned to the greenhouse where watering of the post-emergence phase is done only by subirrigation. The pre-emergence phase is top watered by sprinkling until after test species have emerged. Subsequent watering is by subirrigation.

Two weeks after treatment, the pre- and post-emergence injury and control is rated on a 0–100 percent injury and control scale. Special physiological effects are rated as to intensity also at this time.

The herbicidal test data is reported for Compounds 1–4 and was obtained at application rates ranging from 2 lbs. down to ¼ lb/acre. The following lists the metric equivalents for each rate.

| US - lb./acre | Metric - kg/ha |
|---|---|
| 10.0 | 11.2 |
| 4.0 | 4.48 |
| 2.0 | 2.24 |
| 1.0 | 1.12 |
| 0.5 | 0.56 |
| 0.25 | 0.28 |
| 0.125 | 0.14 |
| 0.0625 | 0.07 |

Test results are set forth in Table I pre-emergence and post-emergence.

TABLE I

| Example No. | Dosage Lbs./Acre | Pre-Emergence | | | | | | | | |
|---|---|---|---|---|---|---|---|---|---|---|
| | | FM | GF | VL | CB | WM | PW | CT | CN | SB |
| 1 | 2 | 100 | 90 | 100 | 50 | 100 | 100 | 70 | 30 | 0 |
| | 1 | 100 | 90 | 90 | 30 | 100 | 100 | 30 | 10 | 0 |
| | ½ | 90 | 10 | 90 | 20 | 100 | 90 | 20 | 0 | 10 |
| | ¼ | 90 | 10 | 80 | 10 | 90 | 90 | 10 | 0 | 0 |
| 2 | 2 | 100 | 100 | 90 | 0 | 100 | 100 | 10 | 20 | 0 |
| | 1 | 100 | 90 | 90 | 10 | 100 | 100 | 20 | 0 | 0 |
| | ½ | 90 | 70 | 80 | 0 | 90 | 100 | 20 | 0 | 0 |
| | ¼ | 90 | 20 | 60 | 0 | 90 | 100 | 10 | 0 | 10 |
| 3 | 2 | 100 | 90 | 50 | 10 | 100 | 100 | 60 | 0 | 0 |
| | ½ | 90 | 50 | 0 | 0 | 50 | 40 | 0 | 0 | 0 |
| | ¼ | — | — | — | — | — | — | — | — | — |
| 4 | 2 | 90 | 70 | 70 | 0 | 100 | 90 | 20 | 0 | 0 |
| | 1 | 90 | 20 | 60 | 0 | 90 | 40 | 10 | 0 | 0 |
| | ½ | 60 | 10 | 40 | 10 | 80 | 20 | 0 | 0 | 0 |

TABLE I-continued

| Example No. | Dosage Lbs./ Acre | Post-Emergence | | | | | | | | |
|---|---|---|---|---|---|---|---|---|---|---|
| | | FM | GF | VL | CB | WM | PW | CT | CN | SB |
| | ¼ | 40 | 10 | 20 | 0 | 60 | 10 | 0 | 0 | 10 |
| 1 | 2 | 90 | 90 | 100 | 100 | 100 | 100 | 100 | 90 | 70 |
| | 1 | 100 | 90 | 100 | 100 | 100 | 100 | 90 | 70 | 50 |
| | ½ | 90 | 90 | 100 | 100 | 100 | 100 | 90 | 60 | 40 |
| | ¼ | 90 | 90 | 70 | 90 | 100 | 100 | 50 | 0 | 30 |
| 2 | 2 | 100 | 100 | 100 | 100 | 100 | 100 | 100 | 90 | 50 |
| | 1 | 100 | 90 | 100 | 100 | 100 | 100 | 100 | 60 | 40 |
| | ½ | 90 | 90 | 100 | 90 | 100 | 100 | 80 | 50 | 40 |
| | ¼ | 90 | 70 | 90 | 90 | 100 | 100 | 70 | 40 | 30 |
| 3 | 2 | 90 | 90 | 100 | 90 | 100 | 100 | 90 | 50 | 60 |
| | ½ | 90 | 90 | 100 | 90 | 100 | 100 | 60 | 10 | 50 |
| | ¼ | 30 | 20 | 90 | 80 | 100 | 100 | 70 | 10 | 10 |
| 4 | 2 | 100 | 100 | 100 | 100 | 100 | 100 | 100 | 80 | — |
| | 1 | 100 | 100 | 100 | 100 | 100 | 100 | 90 | 70 | — |
| | ½ | 90 | 90 | 100 | 90 | 100 | 100 | 90 | 60 | — |
| | ¼ | 90 | 90 | 100 | 90 | 100 | 100 | 70 | 60 | — |

The compounds of the present invention may be particularly advantageous when used to control weeds in field of crops which are relatively tolerant thereto. For instance, the foregoing data demonstrates that certain crop species are more tolerant to these compounds than certain grass or broadleaf weed species. The herbicidal compounds of the present invention are particularly useful when applied in post-emergence applications to control broadleaf weeds, e.g., velvetleaf, cocklebur, wild mustard and pigweed, in soybean fields.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A herbicidal compound of the formula

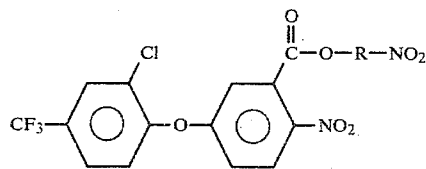

where R is an alkylene group having 1-4 carbon atoms.

2. A herbicidal compound according to claim 1 of the formula

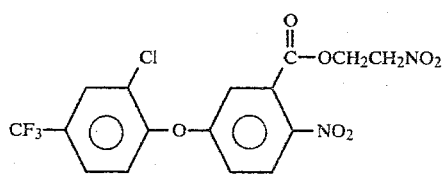

3. A herbicidal compound according to claim 1 of the formula

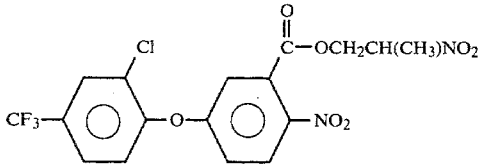

4. A herbicidal compound according to claim 1 of the formula

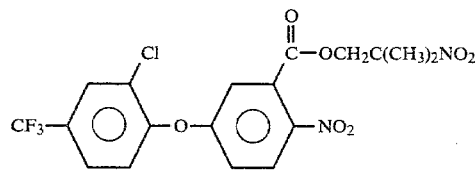

5. A herbicidal compound according to claim 1 of the formula

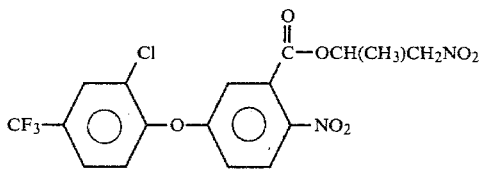

6. A method for combating unwanted plants which comprises contacting them with a herbicidally effective amount of a compound according to any one of claims 1 to 5.

7. A method according to claim 6 wherein said compound is applied in a post-emergence application to a field comprising soybean plants and at least one broadleaf weed species.

8. A method according to claim 7 wherein said broadleaf weed species comprise at least one species selected from the group consisting of velvetleaf, cocklebur, wild mustard and pigweed.

* * * * *

UNITED STATES PATENT AND TRADEMARK OFFICE
CERTIFICATE OF CORRECTION

Page 1 of 2

PATENT NO. : 4,339,268
DATED : July 13, 1982
INVENTOR(S) : Robert J. Theissen

It is certified that error appears in the above-identified patent and that said Letters Patent is hereby corrected as shown below:

Title page, under section (56), insert:

References Cited

U.S. PATENT DOCUMENTS

| | | |
|---|---|---|
| 3,784,635 | 1/1974 | Theissen |
| 3,907,866 | 9/1975 | Theissen |
| 3,983,168 | 9/1976 | Theissen |
| 4,063,929 | 12/1977 | Bayer et al |
| 4,070,178 | 1/1978 | Johnson et al |
| 4,209,318 | 6/1980 | Johnson |
| 4,285,723 | 8/1981 | Cartwright et al |
| 4,070,177 | 1/1978 | Nishiyama et al |

UNITED STATES PATENT AND TRADEMARK OFFICE
CERTIFICATE OF CORRECTION

PATENT NO. : 4,339,268

DATED : July 13, 1982

INVENTOR(S) : Robert J. Theissen

Page 2 of 2

It is certified that error appears in the above-identified patent and that said Letters Patent is hereby corrected as shown below:

| | | |
|---|---|---|
| 4,105,435 | 8/1978 | Nishiyama et al |
| 3,957,852 | 5/1976 | Fujikawa et al |

FOREIGN PATENT DOCUMENTS

| | | |
|---|---|---|
| 1,500,249 | 2/1978 | United Kingdom |
| 151,943 | 11/1979 | Japan |
| 2,058,055A | 4/1981 | United Kingdom |
| 2,049,695A | 12/1980 | United Kingdom |
| 62,637 | 6/1974 | Japan |
| 0,021,692 | 1/1981 | European Patent Convention Publication |

Signed and Sealed this

Seventh Day of December 1982

[SEAL]

Attest:

Attesting Officer

GERALD J. MOSSINGHOFF

Commissioner of Patents and Trademarks

REEXAMINATION CERTIFICATE (1072nd)

United States Patent [19]

Theissen

[11] B1 4,339,268

[45] Certificate Issued  Jun. 6, 1989

[54] HERBICIDAL NITROALKYL 5-[2-CHLORO-4-(TRIFLUOROMETHYL)-PHENOXY]-2-NITROBENZOATES

[75] Inventor: Robert J. Theissen, Bridgewater, N.J.

[73] Assignee: Rhone-Poulenc Agrochimie, Lyons, France

Reexamination Request:
No. 90/000,575, Jun. 14, 1984

Reexamination Certificate for:
Patent No.: 4,339,268
Issued: Jul. 13, 1982
Appl. No.: 271,143
Filed: Jun. 8, 1981

Related U.S. Application Data

[63] Continuation-in-part of Ser. No. 117732, Feb. 1, 1980, abandoned.

[30] Foreign Application Priority Data

Jan. 30, 1981 [AR] Argentina .................. 284163

[51] Int. Cl.$^4$ .................. A01N 37/36; C07C 79/46
[52] U.S. Cl. .................. 71/108; 560/21
[58] Field of Search .................. 560/21; 71/109

[56] References Cited

U.S. PATENT DOCUMENTS 3,137,563  6/1964  Newcomer .................. 71/2.6
3,325,274  6/1967  Anderson .................. 71/2.6

*Primary Examiner*—Paul J. Killos

[57] ABSTRACT

There is provided herbicidal nitroalkyl 5-[2-chloro-4-(trifluoromethyl)phenoxy]-2-nitrobenzoates. These compounds are particularly useful when applied in a post-emergence application to soybean fields containing broadleaf weeds.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-8 is confirmed.

* * * * *